US006649085B2

(12) United States Patent
Reinhardt et al.

(10) Patent No.: US 6,649,085 B2
(45) Date of Patent: Nov. 18, 2003

(54) CYCLIC SUGAR KETONES AS CATALYSTS FOR PEROXYGEN COMPOUNDS

(75) Inventors: Gerd Reinhardt, Kelkheim (DE); Nicole Reichardt, Flörsheim (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/994,091

(22) Filed: Nov. 16, 2001

(65) Prior Publication Data

US 2002/0117649 A1 Aug. 29, 2002

(30) Foreign Application Priority Data

Nov. 25, 2000 (DE) ........................................ 100 58 645

(51) Int. Cl.$^7$ .......................... C07D 311/00; C09K 3/00

(52) U.S. Cl. ............................. 252/186.41; 252/186.4; 549/396

(58) Field of Search ......................... 252/186.41, 186.4; 549/396

(56) References Cited

U.S. PATENT DOCUMENTS

| | | | | |
|---|---|---|---|---|
| 3,822,114 A | | 7/1974 | Montgomery | 252/186.38 |
| 3,979,313 A | | 9/1976 | Nakagawa et al. | 252/186.41 |
| 4,585,642 A | | 4/1986 | Rieck | 423/333 |
| 4,664,839 A | | 5/1987 | Rieck | 252/175 |
| 4,985,553 A | | 1/1991 | Fuertes et al. | 536/124 |
| 5,183,651 A | | 2/1993 | Schimmel et al. | 423/334 |
| 5,229,095 A | | 7/1993 | Schimmel et al. | 423/334 |
| 5,236,682 A | | 8/1993 | Schimmel et al. | 423/334 |
| 5,268,156 A | | 12/1993 | Schimmel et al. | 423/334 |
| 5,308,596 A | | 5/1994 | Kotzian et al. | 423/333 |
| 5,318,733 A | | 6/1994 | Carduck et al. | 264/15 |
| 5,356,607 A | | 10/1994 | Just | 423/334 |
| 5,494,488 A | | 2/1996 | Arnoldi et al. | 910/292 |
| 5,512,206 A | * | 4/1996 | Steltenkamp et al. | 252/186.4 |
| 5,541,316 A | | 7/1996 | Engelskirchen et al. | 510/471 |
| 5,580,941 A | | 12/1996 | Krause et al. | 527/300 |
| 5,616,550 A | | 4/1997 | Kruse et al. | 510/444 |
| 5,785,887 A | | 7/1998 | Steltenkamp et al. | 252/186.42 |
| 5,798,328 A | | 8/1998 | Kottwitz et al. | 510/438 |
| 5,830,956 A | | 11/1998 | Stockhausen et al. | 526/318.2 |

FOREIGN PATENT DOCUMENTS

| | | |
|---|---|---|
| DE | 24 12 837 | 10/1974 |
| DE | 42 21 381 | 2/1994 |
| DE | 43 00 772 | 3/1994 |
| DE | 43 03 320 | 8/1994 |
| DE | 44 16 438 | 11/1995 |
| DE | 44 43 177 | 6/1996 |
| EP | 0 164 514 | 12/1985 |
| EP | 0 232 202 | 8/1987 |
| EP | 0 294 753 | 12/1988 |

(List continued on next page.)

OTHER PUBLICATIONS

English abstract for EP 0294753, Dec. 14, 1988.
English abstract for WO 92/11347, Jul. 9, 1992.
English abstract for JP 4–238809, Aug. 26, 1992.
English abstract for JP 4–260610, Sep. 16, 1992.
English abstract for WO 94/23005, Oct. 13, 1994.
English abstract for DE 4416438, Nov. 16, 1995.
English abstract for DE 4443177, Jun. 13, 1996.
English abstract for WO 97/07191, Feb. 27, 1997.
Roger R. Butterworth, et al., "Selected Methods of Oxidations in Carbohydrate Chemistry", Synthesis, 1971, 19, pp. 70–88.
Hans Grisebach, et al., "Chemistry and Biochemistry of Branched–Chain Sugars", Angew. Chem. Internat. Edit., vol. 11, (1972), No. 3, p. 159–173.
Zhi–Xian Wang, et al., "An Efficient Catalytic Asymmetric Epoxidation Method", J. Am. Chem. Soc., 1997, 119, pp. 11224–11235.
Zhi–Xian Wang, et al., "A Dramatic pH Effect Leads to a Catalytic Asymmetric Epoxidation", 1997, 62, pp. 2328–2329.
Waldemar Adam, et al., "Enantioselective oxidation of vic–diols to optically active α–hydroxy ketones by a fructose–derived dioxirane", Tetrahedron: Asymmetry 9, (1998), pp. 4117–4122.
Waldemar Adam, et al., "Asymmetric epoxidation of olefins by chiral dioxiranes generated in situ from ketones of D–(–)–quinic acid", Tetrahedron: Asymmetry 10, (1999), pp. 2749–2755.
EPO Search Report for application No. 01127186, mail date Apr. 8, 2002.

*Primary Examiner*—Alan L. Rotman
*Assistant Examiner*—Raymond Covington
(74) *Attorney, Agent, or Firm*—Richard P. Silverman

(57) ABSTRACT

The use of cyclic sugar ketones of the formula

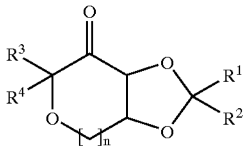

in which $R^1$ and $R^2$ are hydrogen, $C_1$–$C_{22}$-alkyl, $C_2$–$C_{22}$-alkenyl or phenyl, $R^3$ is $C_1$–$C_4$-alkoxy, phenyl-$CH_2$—O— or a group of the formula

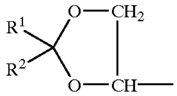

$R^4$ is hydrogen or $R^3$ and $R^4$ together are a group of the formula

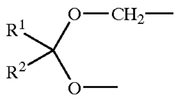

and n is zero or 1, as catalysts for peroxygen compounds.

9 Claims, No Drawings

FOREIGN PATENT DOCUMENTS

| | | |
|---|---|---|
| EP | 0 392 592 | 10/1990 |
| EP | 0 425 427 | 5/1991 |
| EP | 0 425 428 | 5/1991 |
| EP | 0 436 835 | 7/1991 |
| EP | 0 443 651 | 8/1991 |
| EP | 0 448 337 | 9/1991 |
| EP | 0 458 397 | 11/1991 |
| EP | 0 486 592 | 5/1992 |
| EP | 0 502 325 | 9/1992 |
| EP | 0 544 490 | 6/1993 |
| EP | 0 548 599 | 6/1993 |
| EP | 0 549 271 | 6/1993 |
| EP | 0 630 964 | 12/1994 |
| EP | 0 642 576 | 3/1995 |
| GB | 1 464 427 | 2/1977 |
| JP | 4-238809 | 8/1992 |
| JP | 4-260610 | 9/1992 |
| WO | 91/08171 | 6/1991 |
| WO | 92/11347 | 6/1992 |
| WO | 92-18542 | 10/1992 |
| WO | 93/16110 | 8/1993 |
| WO | 94/02597 | 2/1994 |
| WO | 94/02618 | 2/1994 |
| WO | 94/18314 | 8/1994 |
| WO | 94/23005 | 10/1994 |
| WO | 94/23053 | 10/1994 |
| WO | 95/07331 | 3/1995 |
| WO | 95/07350 | 3/1995 |
| WO | 95/19953 | 7/1995 |
| WO | 95/19954 | 7/1995 |
| WO | 95/19955 | 7/1995 |
| WO | 95/22592 | 8/1995 |
| WO | 95/31527 | 11/1995 |
| WO | 97/07191 | 2/1997 |

* cited by examiner

CYCLIC SUGAR KETONES AS CATALYSTS FOR PEROXYGEN COMPOUNDS

FIELD OF THE INVENTION

The present invention relates to the use of certain cyclic sugar ketones for enhancing the bleaching action of peroxygen compounds during the bleaching of colored soilings both on textiles and also on hard surfaces, and to laundry detergents and cleaners which comprise such cyclic sugar ketones.

BACKGROUND OF THE INVENTION

Inorganic peroxygen compounds, in particular hydrogen peroxide and solid peroxygen compounds which dissolve in water to liberate hydrogen peroxide, such as sodium perborate and sodium carbonate perhydrate, have been used for a long time as oxidizing agents for disinfection and bleaching purposes. The oxidation effect of these substances depends heavily on the temperature in dilute solutions; thus, for example, using $H_2O_2$ or perborate in alkaline bleach liquors, a sufficiently rapid bleaching of soiled textiles is achieved only at temperatures above approximately 80° C.

At lower temperatures, the oxidation effect of the inorganic peroxygen compounds can be improved by adding "bleach activators". For this purpose, numerous proposals have been worked out in the past, primarily from the substance classes of N- or O-acyl compounds, for example polyacylated alkylenediamines, in particular tetraacetylglycoluril, N-acylated hydantoins, hydrazides, triazoles, hydrotriazines, urazoles, diketopiperazines, sulfurylamides and cyanurates, and also carboxylic anhydrides, in particular phthalic anhydride and substituted maleic anhydrides, carboxylic esters, in particular sodium nonanoyloxybenzenesulfonate (NOBS), sodium isononanoyloxybenzenesulfonate (ISONOBS) and acylated sugar derivatives, such as pentaacetylglucose. By adding these substances it is possible to increase the bleaching action of aqueous peroxide solutions to the extent that even at temperatures around 60° C. essentially the same effects arise as with the peroxide solution on its own at 95° C.

In efforts for energy-saving washing and bleaching processes, use temperatures significantly below 60° C., in particular below 45° C. down to cold-water temperature have gained in importance in recent years. At these low temperatures, the effect of the activator compounds known hitherto usually noticeably decreases. There has therefore been no lack of attempts to develop more effective activators for this temperature range although hitherto a convincing success has not been recorded.

A starting point for this arises from the use of transition metal salts and complexes thereof, as are described, for example, in EP 0 392 592, EP 0 443 651, EP 0 458 397, EP 0 544 490 or EP 0 549 271. EP 0 630 964 discloses certain manganese complexes which, despite not having a marked effect with regard to a bleach boosting of peroxygen compounds and not decoloring textile fibers, are able to effect bleaching of soil or dye detached from the fiber and present in wash liquors. DE 44 16 438 discloses manganese, copper and cobalt complexes which can carry ligands from a large number of groups of substances and are reportedly used as bleach and oxidation catalysts. WO 97/07191 proposes complexes of manganese, iron, cobalt, ruthenium and molybdenum with ligands of the salene type as activators for peroxygen compounds in cleaning solutions for hard surfaces. The use of metal-containing bleach activators, however, frequently has the disadvantage that damage to the textile fabric can arise under unfavorable conditions.

The literature also describes metal-free bleach catalysts. Thus, U.S. Pat. No. 3,822,114, for example, describes bleaches which, in addition to an organic or inorganic peroxygen compound, comprise ketones or aldehydes as bleach boosters. U.S. Pat. No. 3,822,114 teaches, in tables 2, 3, 4 and 5, the use of a large number of cyclic and open-chain ketones which have good effectiveness at temperatures above 80° F. However, there is neither indications that ketones based on sugar can be used, nor that these are already effective at temperatures below 80° F. WO 95/31527 describes bi- and tricyclic ketones as bleach activators. Decalin-1,5-dione, methyldecalin-1,6-dione and tricycloundecanediones are mentioned as examples. Also described in U.S. Pat. No. 5,785, 887 are open-chain or cyclic monoketals of diketones such as cyclohexanedione as bleach activators. This specification does not give information on ketones based on sugar either.

The aim of the present invention is to improve the oxidation and bleaching action, in particular of inorganic peroxygen compounds, at low temperatures below 80° C., in particular in the temperature range from about 5° C. to 45° C.

SUMMARY OF THE INVENTION

Surprisingly, it has now been found that certain keto group-carrying sugars, in the presence of organic or inorganic peroxygen compounds, contribute significantly to the cleaning performance toward colored soilings present on textiles or on hard surfaces.

The invention provides for the use of cyclic sugar ketones of the formula

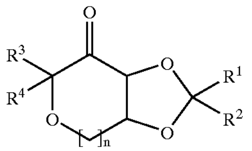

in which $R^1$ and $R^2$ are hydrogen, $C_1$–$C_{22}$-alkyl, $C_2$–$C_{22}$-alkenyl or phenyl, $R^3$ is $C_1$–$C_4$-alkoxy, phenyl-$CH_2$—O— or a group of the formula

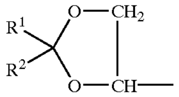

$R^4$ is hydrogen or $R^3$ and $R^4$ together are a group of the formula

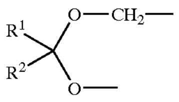

and n is zero or 1, as catalysts for peroxygen compounds.

DETAILED DESCRIPTION OF THE INVENTION

Corresponding sugar ketones are described, for example, in Z. -X. Wang et al., J. Org. Chem., 1997, 62, 2328–2329, Z. -X. Wang et al., J. Amer. Chem. Soc., 1997, 119, 11224–11235, W. Adam et al., Tetrahedron Asymmetry, 1999,10, 2749–2755 and 1998, 9, 4117–4122. As is known to the person skilled in the art, the ketones can be obtained by acetalation or ketalation of the corresponding sugars and subsequent oxidation of an alcohol function. Oxidation reactions are described, for example, in R. F. Butterworth and S. Hanessian, Synthesis, 1971, 19 and P. H. Grisebach and H. Schmid, Angew. Chem., Int. Ed. Engl., 1972, 11, 159.

As is known from J. Amer. Chem. Soc., 1997, 119, 11224–11235, the sugar ketones can form dioxirane structures in aqueous solution in the presence of peroxy compounds in accordance with the following reaction equation:

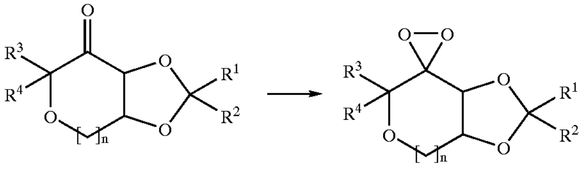

These dioxirane compounds represent the actual bleaching agent.

Particularly preferred sugar ketones are:

1,2:4,5-di-O-isopropylidene-D-erythro-2,3-hexodiuro-2,6-pyranose, 1,2:4,5-di-O-isopropylidene-L-erythro-2,3-hexodiuro-2,6-pyranose, 1,2:5,6-di-O-isopropylidene-α-D-glucofuranos-3-ulose hydrate, methyl-3,4-O-isopropylidene-β-L-erythropentopyranosid-2-ulose.

Also particularly preferred are the pyranose derivatives of the following formulae 1 to 3, and their lower homologs with $C_2$-, $C_3$-, $C_4$-, $C_5$-, $C_6$- or $C_7$- instead of the $C_8$-radical:

(1)

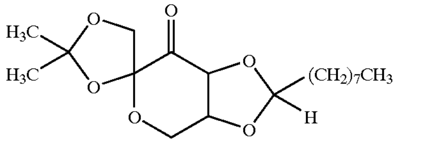

(2)

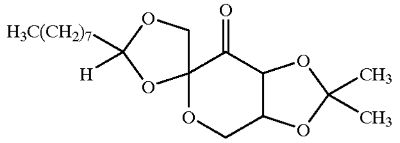

(3)

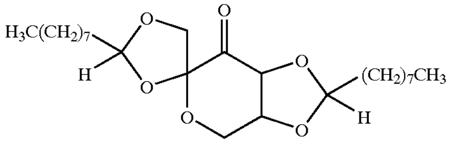

The cyclic sugar ketones are used in the laundry detergents and cleaners according to the invention, which also comprise organic or inorganic peroxygen compounds, in concentrations of 0.01–10%, preferably 0.1–8% and in particular 0.5–5%.

Suitable peroxygen compounds are primarily all alkali metal or ammonium peroxosulfates, such as, for example, potassium peroxomonosulfate (industrially: Caroat® or Oxone®). However, it is also possible to use alkali metal perborate mono- or tetrahydrates and/or alkali metal percarbonates, where sodium is the preferred alkali metal. In a particularly preferred embodiment, mixtures of peroxosulfates with perborates or percarbonates in the mixing ratio 1:10 to 10:1, preferably 1:5 to 5:1 are used. The concentration of the inorganic oxidizing agents in the overall formulation of the cleaner is 5–90%, preferably 10–70%.

Additionally or alternatively, the cleaners according to the invention can comprise oxidizing agents on an organic basis in the concentration range 1–20%. These include all known peroxycarboxylic acids, e.g. monoperoxyphthalic acid, dodecanediperoxy acid or phthalimidoperoxycarboxylic acids such as PAP.

The term bleaching is understood here as meaning both the bleaching of soil on the textile surface and the bleaching of soil detached from the textile surface and present in the wash liquor. Analogous statements apply for the bleaching of soilings on hard surfaces. Further potential uses are in the personal care sector, e.g. in the bleaching of hair and for improving the effectiveness of denture cleansers. Furthermore, the complexes according to the invention are used in commercial laundries, in the bleaching of wood and paper, the bleaching of cotton and in disinfectants.

Furthermore, the invention relates to a laundry detergent and cleaner such as, for example, laundry detergents and bleaches for textile material, cleaners for hard surfaces, such as dishwashing detergents or denture cleansers, which comprise the sugar ketones as defined above and peroxygen compounds.

The use of the sugar ketones as bleach catalysts consists essentially in providing conditions in the presence of a hard surface contaminated with colored soilings, or a correspondingly soiled textile, under which a peroxidic oxidizing agent and the cyclic sugar ketone can react with one another, with the aim of obtaining more strongly oxidizing subsequent products having a dioxirane structure. Such conditions arise particularly if the reactants meet in aqueous solution. This can arise by separately adding the peroxygen compound and the sugar ketone to a solution which may contain laundry detergent or cleaner. Particularly advantageously, the laundry detergent or cleaner comprises the cyclic sugar ketone and optionally a peroxygen-containing oxidizing agent from the outset. The peroxygen compound can also be added to the solution separately without diluent or, preferably, as an aqueous solution or suspension if a peroxygen-free laundry detergent or cleaner is used.

The laundry detergents and cleaners according to the invention, which can be in the form of granules, pulverulent or tableted solids, as other moldings, homogeneous solutions or suspensions, can in principle comprise all ingredients known and customary in such compositions in addition to said cyclic ketone. The laundry detergents and cleaners according to the invention can, in particular, comprise builder substances, surfactants, peroxygen compounds, additional peroxygen activators or organic peracids, water-miscible organic solvents, sequestering agents, enzymes, and specific additives with an action which is gentle on colors and fibers. Further auxiliaries, such as electrolytes, pH regulators, silver corrosion inhibitors, foam regulators and dyes and fragrances, are possible.

A hard-surface cleaner according to the invention can moreover comprise abrasive constituents, in particular from the group consisting of quartz flours, wood flours, plastic flours, chalks and micro glass beads, and mixtures thereof. Abrasive substances are preferably present in the cleaners according to the invention in amounts not exceeding 20% by weight, in particular from 5 to 15% by weight.

The laundry detergents and cleaners can comprise one or more surfactants, suitable surfactants being, in particular, anionic surfactants, nonionic surfactants, and mixtures thereof, and also cationic, zwitterionic and amphoteric surfactants. Such surfactants are present in laundry detergents according to the invention in amounts of preferably 1 to 50% by weight, in particular from 3 to 30% by weight, whereas in hard-surface cleaners, lesser amounts, i.e. amounts up to 20% by weight, in particular up to 10% by weight and preferably in the range from 0.5 to 5% by weight, are normally present. In cleaners for use in machine dishwashing processes, low-foam compounds are normally used.

Suitable anionic surfactants are, in particular, soaps and those which contain sulfate or sulfonate groups. Suitable surfactants of the sulfonate type are preferably $C_9$–$C_{13}$-alkylbenzenesulfonates, olefinsulfonates, i.e. mixtures of alkene- and hydroxyalkanesulfonates, and disulfonates, as are obtained, for example, from monoolefins with terminal or internal double bond by sulfonation with gaseous sulfur trioxide and subsequent alkaline or acidic hydrolysis of the sulfonation products. Also suitable are alkanesulfonates obtained from $C_{12}$–$C_{18}$-alkanes, for example by sulfochlorination or sulfoxidation with subsequent hydrolysis or neutralization. Also suitable are the esters of alpha-sulfofatty acids (ester sulfonates), for example the alpha-sulfonated methyl esters of hydrogenated coconut, palm kernel or tallow fatty acids which are prepared by sulfonation of the methyl esters of fatty acids of vegetable and/or animal origin having 8 to 20 carbon atoms in the fatty acid molecule, and subsequent neutralization to give water-soluble monosalts.

Further suitable anionic surfactants are sulfated fatty acid glycerol esters, which are mono-, di- and triesters, and mixtures thereof. Preferred alk(en)yl sulfates are the alkali metal and, in particular, the sodium salts of sulfuric monoesters of $C_{12}$–$C_{18}$-fatty alcohols, for example from coconut fatty alcohol, tallow fatty alcohol, lauryl, myristyl, cetyl or stearyl alcohol or of $C_8$–$C_{20}$-oxo alcohols and those monoesters of secondary alcohols of this chain length. Also preferred are alk(en)yl sulfates of said chain length which contain a synthetic straight-chain alkyl radical prepared on a petrochemical basis. 2,3-Alkyl sulfates, which are prepared, for example, in accordance with the US American patents U.S. Pat. No. 3,234,158 and the U.S. Pat. No. 5,075,041, are suitable anionic surfactants. Also suitable are the sulfuric monoesters of the straight-chain or branched alcohols ethoxylated with 1 to 6 mol of ethylene oxide, such as 2-methyl-branched $C_9$–$C_{11}$-alcohols having, on average, 3.5 mol of ethylene oxide (EO) or $C_{12}$–$C_{18}$-fatty alcohols having 1 to 4 EO.

Preferred anionic surfactants also include the salts of alkylsulfosuccinic acid, which are also referred to as sulfosuccinates or as sulfosuccinic esters and which are monoesters and/or diesters of sulfosuccinic acid with alcohols, preferably fatty alcohols and, in particular, ethoxylated fatty alcohols. Preferred sulfosuccinates contain $C_8$–$C_{18}$-fatty alcohol radicals or mixtures thereof. Other suitable anionic surfactants are fatty acid derivatives of amino acids, for example of n-methyltaurin (taurides) and/or of N-methylglycine (sarcosinates). Further suitable anionic surfactants are, in particular, soaps, for example in amounts of from 0.2 to 5% by weight. In particular, saturated fatty acid soaps, such as the salts of lauric acid, myristic acid, palmitic acid, stearic acid, hydrogenated erucic acid and behenic acid, and, in particular, soap mixtures derived from natural fatty acids, for example coconut, palm kernel or tallow fatty acids, are suitable.

The anionic surfactants, including the soaps, can be present in the form of their sodium, potassium or ammonium salts, and as soluble salts of organic bases, such as mono-, di- or triethanolamines. The anionic surfactants are preferably in the form of their sodium or potassium salts, in particular in the form of the sodium salts. Anionic surfactants are present in laundry detergents according to the invention preferably in amounts of from 0.5 to 10% by weight and, in particular, in amounts of from 5 to 25% by weight.

The nonionic surfactants used are preferably alkoxylated, advantageously ethoxylated, in particular primary, alcohols having, preferably, 8 to 18 carbon atoms and, on average, 1 to 12 mol of ethylene oxide (EO) per mole of alcohol, in which the alcohol radical may be linear or, preferably, methyl-branched in the 2-position, or may comprise a mixture of linear and methyl-branched radicals, as are usually present in oxo alcohol radicals. However, particular preference is given to alcohol ethoxylates with linear radicals from alcohols of a native origin having 12 to 18 carbon atoms, e.g. from coconut, palm, tallow fatty or oleyl alcohol, and, on average, 2 to 8 EO per mole of alcohol. Preferred ethoxylated alcohols include, for example, $C_{12}$–$C_{14}$-alcohols having 3 EO or 4 EO, $C_9$–$C_{11}$-alcohols having 7 EO, $C_{13}$–$C_{15}$-alcohols having 3 EO, 5 EO, 7 EO or 8 EO, $C_{12}$–$C_{18}$-alcohols having 3 EO, 5 EO or 7 EO and mixtures thereof, such as mixtures of $C_{12}$–$C_{14}$-alcohol with 3 EO and $C_{12}$–$C_{18}$-alcohol with 7 EO. The stated degrees of ethoxylation are statistical average values which, for a specific product, may be an integer or a fraction. Preferred alcohol ethoxylates have a narrowed homolog distribution (narrow range ethoxylates, NRE). In addition to the nonionic surfactants, it is also possible to use fatty alcohols having more than 12 EO. Examples thereof are (tallow) fatty alcohols having 14 EO, 16 EO, 20 EO, 25 EO, 30 EO or 40 EO.

The nonionic surfactants also include alcohol glycosides of the formula $RO(G)_x$ in which R is a primary straight-chain or methyl-branched, in particular methyl-branched in the 2-position, aliphatic radical having 8 to 22, preferably 12 to 18, carbon atoms and G is a glycose unit having 5 or 6 carbon atoms, preferably glucose. The degree of oligomerization x, which gives the distribution of monoglycosides and oligoglycosides, is any desired number, which, being an analytically determined parameter, can also assume fractional values—is between 1 and 10; x is preferably 1.2 to 1.4. Likewise suitable are polyhydroxyfatty acid amides of the formula (I)

(1)

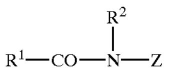

in which the radical $R^1$-CO is an aliphatic acyl radical having 6 to 22 carbon atoms, $R^2$ is hydrogen; an alkyl or hydroxyalkyl radical having 1 to 4 carbon atoms and [Z] is a linear or branched polyhydroxyalkyl radical having 3 to 10 carbon atoms and 3 to 10 hydroxyl groups. The polyhydroxyfatty acid amides are preferably derived from reducing sugars having 5 or 6 carbon atoms, in particular from glucose. The group of polyhydroxyfatty acid amides also includes compounds of the formula (II)

(II)

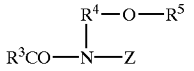

in which $R^3$ is a linear or branched alkyl or alkenyl radical having 7 to 21 carbon atoms, $R^4$ is a linear, branched or cyclic alkylene radical or an arylene radical having 6 to 8 carbon atoms and $R^5$ is a linear, branched or cyclic alkyl radical or an aryl radical or an oxy-alkyl radical having 1 to 8 carbon atoms, where $C_1$–$C_4$-alkyl or phenyl radicals are preferred, and [Z] is a linear polyhydroxyalkyl radical whose alkyl chain is substituted by at least two hydroxyl groups, or alkoxylated, preferably ethoxylated or propoxylated derivatives of this radical. [Z] is here, too, preferably obtained by reductive amination of a sugar such as glucose, fructose, maltose, lactose, galactose, mannose or xylose. The N-alkoxy- or -N-alyloxy-substituted compounds can then be converted into the desired polyhydroxyfatty acid amides, for example in accordance with WO 95/07331 by reaction with fatty acid methyl esters in the presence of an alkoxide as catalyst.

A further class of preferred nonionic surfactants, which are used either as the sole nonionic surfactant or in combination with other nonionic surfactants, in particular together with alkoxylated fatty alcohols and/or alkyl glycosides, are alkoxylated, preferably ethoxylated or ethoxylated and propoxylated, fatty acid alkyl esters, preferably having 1 to 4 carbon atoms in the alkyl chain, in particular fatty acid methyl esters.

Non ionic surfactants of the amine oxide type, for example N-cocoalkyl-N,N-dimethylamine oxide and N-tallow-alkyl-N,N-dihydroxyethylamine oxide, and of the fatty acid alkanolamide type may also be suitable.

Other suitable surfactants are "gemini surfactants". These are generally understood as meaning compounds which have two hydrophilic groups per molecule. These groups are usually separated from one another by a "spacer". This spacer is usually a carbon chain which should be long enough for the hydrophilic groups to have a sufficient distance such that they can act independently of one another. Such surfactants are generally characterized by an unusually low critical micelle concentration and the ability to drastically reduce the surface tension of water. However, it is also possible to use gemini polyhydroxyfatty acid amides or poly-polyhydroxyfatty acid amides, as described in international patent applications WO 95/19953, WO 95/19954 and WO 95/19955. Further surfactant types can have dendrimeric structures.

A laundry detergent according to the invention preferably comprises at least one water-soluble and/or water-insoluble, organic and/or inorganic builder.

Suitable water-soluble inorganic builder materials are, in particular, alkali metal silicates and polymeric alkali metal phosphates, which can be in the form of their alkaline, neutral or acidic sodium or potassium salts. Examples thereof are trisodium phosphate, tetrasodium diphosphate, disodium dihydrogen diphosphate, pentasodium triphosphate, "sodium hexametaphosphate", and the corresponding potassium salts, or mixtures of sodium and potassium salts. Suitable water-insoluble, water-dispersible inorganic builder materials used are, in particular, crystalline or amorphous alkali metal alumosilicates, in particular in amounts of up to 50% by weight. Of these, the crystalline sodium alumosilicates in laundry detergent quality, in particular zeolite A, P and optionally X, alone or in mixtures, for example in the form of a cocrystallisate of the zeolites A and X, are preferred. Their calcium-binding capacity, which can be determined in accordance with the instructions in German patent DE 24 12 837, is usually in the range from 100 to 200 mg, of CaO per gram. Suitable builder substances are also crystalline alkali metal silicates, which can be present alone or in mixtures with amorphous silicates. The alkali metal silicates which can be used as builders preferably have a molar ratio of alkali metal oxide to $SiO_2$ below 0.95, in particular of 1:1.1 to 1:12 and can be in amorphous or crystalline form. Preferred alkali metal silicates are the sodium silicates, in particular the amorphous sodium silicates having a molar ratio of $Na_2O:SiO_2$ or 1:2 to 1:2.8. Those with an $Na_2O:SiO_2$ molar ratio from 1:1.9 to 1:2.8 can be prepared by the process of European patent application EP 0 425 427. The crystalline silicates used, which can be present alone or as a mixture with amorphous silicates, are preferably crystalline phyllosilicates of the formula $Na_2Si_xO_{2x+1}.Y\ H_2O$, in which x, the "modulus", is a number from 1.9 to 4 and y is a number from 0 to 20, and preferred values for x are 2, 3 or 4. Crystalline phyllosilicates which fall under this formula are described, for example, in European patent application EP 0 164 514. Preferred crystalline phyllosilicates are those in which x in said general formula assumes the values 2 or 3. Particular preference is given to both β- and β-sodium disilicates ($Na_2Si_2O_5.y\ H_2O$), where β-sodium disilicate can be obtained, for example, according to the process described in international patent application WO 91/08171. β-Sodium silicates with a modulus between 1.9 and 3.2 can be prepared in accordance with Japanese patent applications JP 04/238 809 or JP 04/260 6 10. Virtually anhydrous crystalline alkali metal silicates prepared from amorphous silicates and of the abovementioned formula in which x is a number from 1.9 to 2.1, which can be prepared as described in European patent applications EP 0 548 599, EP 0 502 325 and EP 0 425 428, can also be used. In a further preferred embodiment of such compositions, a crystalline sodium phyllosilicate with a modulus of from 2 to 3 is used, as can be prepared in accordance with the process of European patent application EP 0 436 835 from sand and soda. Crystalline sodium silicates with a modulus in the range from 1.9 to 3.5, as are obtainable in accordance with the processes of European patents EP 0 164 552 and/or EP 0 294 753, are used in a further preferred embodiment of compositions according to the invention. In a preferred embodiment of compositions according to the invention, a granular compound of alkali metal silicate and alkali metal carbonate, as listed, for example, in international patent application WO 95/22592 or as is commercially available, for example, under the name Nabion®, is used. In cases where alkali metal alumosilicate, in particular zeolite, is present as additional builder substance, the weight ratio of alumosilicate to silicate, in each case based on anhydrous active substances, is preferably 1:10 to 10:1. In compositions which comprise both amorphous and crystalline alkali metal silicates, the weight ratio of amorphous alkali metal silicate to crystalline alkali metal silicate is preferably 1:2 to 2:1 and in particular 1:1 to 2:1.

Such builder substances are present in compositions according to the invention preferably in amounts of up to 60% by weight, in particular from 5 to 40% by weight.

The water-soluble organic builder substances include polycarboxylic acids, in particular citric acid and sugar acids, aminopolycarboxylic acids, in particular methylglycinediacetic acid, nitrilotriacetic acid and ethylenediaminetetraacetic acid, and polyaspartic acid.

Polyphosphonic acids, in particular aminotris (methylenephosphonic acid), ethylenediaminetetrakis (methylenephosphonic acid) and 1-hydroxyethane-1,1-diphosphonic acid, can likewise be used. Preference is also given to polymeric (poly)carboxylic acids, in particular the polycarboxylates of international patent application WO 93/161 10 or of international patent application WO 92/18542 or of European patent application EP 0 232 202, accessible by oxidation of polysaccharides or dextrins, polymeric acrylic acids, methacrylic acids, maleic acids and mixed polymers thereof, which may also comprise small amounts of polymerizable substances without carboxylic acid functionality in copolymerized form. The relative molecular mass of the homopolymers of unsaturated carboxylic acids is generally between 5 000 and 200 000, that of the copolymers is between 2 000 and 200 000, preferably 50 000 to 120 000, in each case based on free acid. A particularly preferred acrylic acid-maleic acid copolymer has a relative molecular mass of from 50 000 to 100 000. Commercially available products are for example, Sokalan® CP 5, CP 10 and PA 30 from BASF. Also suitable are copolymers of acrylic acid or methacrylic acid with vinyl ethers, such as vinyl methyl ethers, vinyl esters, ethylene, propylene and styrene, in which the proportion of acid is at least 50% by weight. Other water-soluble organic builder substances which may be used are terpolymers which contain, as monomers, two unsaturated acids and/or salts thereof, and, as a third monomer, vinyl alcohol and/or an esterified vinyl alcohol or a carbohydrate. The first acidic monomer or salt thereof is derived from a monoethylenically unsaturated $C_3$–$C_8$-carboxylic acid and preferably from a $C_3$–$C_4$-monocarboxylic acid, in particular from (meth) acrylic acid.

The second acidic monomer or salt thereof can be a derivative of a $C_4$–$C_8$-dicarboxylic acid, maleic acid being particularly preferred, and/or a derivative of an allylsulfonic acid which is substituted in the 2-position by an alkyl or aryl radical. Such polymers can be prepared, in particular, according to processes described in German patent DE 42 21 381 and DE 43 00 772, and generally have a relative molecular mass between 1 000 and 200 000. Further preferred copolymers are those which are described in German patent applications DE 43 03 320 and DE 44 17 734 and have, as monomers, preferably acrolein and acrylic acid/acrylic acid salts or vinyl acetate.

The organic builder substances can, in particular for the preparation of liquid compositions, be used in the form of aqueous solutions, preferably in the form of 30 to 50% strength by weight aqueous solutions. All said acids are usually used in the form of their water-soluble salts, in particular their alkali metal salts. Such organic builder substances can, if desired, be present in amounts up to 40% by weight, in particular up to 25% by weight and preferably from 1 to 8% by weight. Amounts close to said upper limit are preferably used in paste or liquid, in particular water-containing, compositions.

Suitable water-soluble builder components in hard-surface cleaners according to the invention are, in principle, all builders customarily used for machine dishwashing, for example the abovementioned alkali metal phosphates. Their amounts can be in the range up to about 60% by weight, in particular 5 to 20% by weight, based on the overall composition. Further possible water-soluble builder components are, as well as polyphosphonates and phosphonate alkyl carboxylates, for example organic polymers of native or synthetic origin of the polycarboxylate type listed above which, particularly in hard-water regions, act as cobuilders, and naturally occurring hydroxycarboxylic acids, such as, for example, mono-, dihydroxysuccinic acid, alpha-hydroxypropionic acid and gluconic acid. Preferred organic builder components include the salts of citric acid, in particular sodium citrate. Suitable as sodium citrate are anhydrous trisodium citrate and, preferably, trisodium citrate dihydrate. Trisodium citrate dihydrate can be used as a finely or coarsely crystalline powder. Depending on the pH ultimately set in the cleaners according to the invention, the acids corresponding to said cobuilder salts may also be present.

In addition to the sugar ketones used according to the invention, it is possible to use conventional bleach activators, i.e. compounds which release peroxocarboxylic acids under perhydrolysis conditions. The customary bleach activators which contain O- and/or N-acyl groups are suitable. Preference is given to polyacylated alkylenediamines, in particular tetraacetylethylenediamine (TAED), acylated glycolurils, in particular tetraacetylglycoluril (TAGU), acylated triazine derivatives, in particular 1,5-diacetyl-2,4-dioxohexahydro-1,3,5-triazine (DADHT), acylated phenylsulfonates, in particular nonanoyl- or isononanoyloxybenzenesulfonate (NOBS and ISONOBS), respectively, acylated polyhydric alcohols, in particular triacetin, ethylene glycol diacetate and 2,5-diacetoxy-2,5-dihydrofuran, and acylated sorbitol and mannitol, and acylated sugar derivatives, in particular pentaacetylglucose (PAG), pentaacetylfructose, tetraacetylxylose and octaacetyllactose, and acylated, optionally N-alkylated glucamine and gluconolactone. It is also possible to use the combinations of conventional bleach activators known from German patent application DE 44 43 177.

The enzymes optionally present in the compositions according to the invention include proteases, amylases, pullulanases, cellulases, cutinases and/or lipases, for example proteases such as BLAP®, Optimase®, Opticlean®, Maxacal®, Maxapem®, Durazym®, Purafect® OxP, Esperase® and/or Savinase®, amylases such as Termamyl®, Amylase-LT, Maxamyl®, Duramyl®, Purafectel OxAm, cellulases such as Celluzyme®, Carezyme®, K-AC® and/or the cellulases and/or lipases known from international patent applications WO 96/34108 and WO 96/34092, such as Lipolase®, Lipomax®, Lumafast® and/or Lipozym®. The enzymes used can, as described, for example, in international patent applications WO 92111347 or WO 94/23005, be adsorbed to carrier substances and/or embedded in coating substances in order to protect them from premature deactivation. They are present in laundry detergents and cleaners according to the invention preferably in amounts up to 10% by weight, in particular from 0.05 to 5% by weight, particular preference being given to using enzymes stabilized against oxidative degradation, as are known, for example, from international patent applications WO 94/02597, WO 94/02618, WO 94/18314, WO 94/23053 or WO 95/07350.

Machine dishwashing detergents according to the invention preferably comprise the customary alkali metal carriers, such as, for example, alkali metal silicates, alkali metal carbonates and/or alkali metal hydrogencarbonates. The customarily used alkali metal carriers include carbonates, hydrogencarbonates and alkali metal silicates with an $SiO_2$/$M_2O$ molar ratio (M=alkali metal atom) of from 1:1 to 2.5:1. Alkali metal silicates can be present in amounts of up to 40% by weight, in particular 3 to 30% by weight, based on the overall composition. The alkali metal carrier system preferably used in cleaners according to the invention is a mixture of carbonate and hydrogencarbonate, preferably sodium carbonate and sodium hydrogencarbonate, which may be present in an amount of up to 50% by weight, preferably 5 to 40% by weight.

The invention further provides a composition for machine dishwashing, comprising 15 to 65% by weight, in particular 20 to 60% by weight, of water-soluble builder component, 5 to 25% by weight, in particular 8 to 17% by weight, of oxygen-based bleaches, in each case based on the overal composition, and 0.1 to 5% by weight of one or more of the above-defined cyclic sugar ketones. Such a composition preferably has low alkalinity, i.e. its percentage strength by weight solution has a pH of from 8 to 11.5, in particular 9 to 11.

In a further embodiment of compositions according to the invention for automatic dishwashing, 20 to 60% by weight of water-soluble organic builders, in particular alkali metal citrate, 3 to 20% by weight of alkali metal carbonate and 3 to 40% by weight of alkali metal disilicate are present.

In order to effect silver corrosion protection, silver corrosion inhibitors can be used in dishwashing detergents according to the invention. Preferred silver corrosion protectants are organic sulfides, such as cystine and cysteine, di- or trihydric phenols, optionally alkyl- or aryl-substituted triazoles, such as benzotriazole, isocyanuric acid, titanium, zirconium, hafnium, molybdenum, vanadium or cerium salts and/or complexes, and salts and/or complexes of the metals present in the complexes suitable according to the invention, with ligands other than those given in formula (I).

If the compositions foam excessively upon use, up to 6% by weight, preferably about 0.5 to 4% by weight, of a foam-regulating compound, preferably from the group consisting of silicones, paraffins, paraffin/alcohol combinations, hydrophobicized silicas, bisfatty acid amides and mixtures thereof and other further known commercially available foam inhibitors, can also be added. Preferably, the foam inhibitors, in particular silicone- and/or paraffin-containing foam inhibitors, are bonded to a granular water-soluble or -dispersible carrier substance. In this connection, particular preference is given to mixtures of paraffins and bistearylethylenediamide. Other possible ingredients in the compositions according to the invention are, for example, perfume oils.

The organic solvents which can be used in the compositions according to the invention, particularly if they are in liquid or paste form, include alcohols having 1 to 4 carbon atoms, in particular methanol, ethanol, isopropanol and tert-butanol, diols having 2 to 4 carbon atoms, in particular ethylene glycol and propylene glycol, and mixtures thereof and the ethers derivable from said classes of compound. Such water-miscible solvents are present in the cleaners according to the invention preferably in amounts not exceeding 20% by weight, in particular from 1 to 15% by weight.

To set a desired pH which does not arise by itself as a result of mixing the other components, the compositions according to the invention can comprise system- and environment-compatible acids, in particular citric acid, acetic acid, tartaric acid, malic acid, lactic acid, glycolic acid, succinic acid, glutaric acid and/or adipic acid and also mineral acids, in particular sulfuric acid or alkali metal hydrogensulfates, or bases, in particular ammonium or alkali metal hydroxides. Such pH regulators are present in the compositions according to the invention preferably in amounts not exceeding 10% by weight, in particular from 0.5 to 6% by weight.

The compositions according to the invention are preferably compositions in the form of powders, granules or tablets, which can be prepared in a manner known per se, for example by mixing, granulation, roll compaction and/or spraydrying of the thermally stable components and mixing in the more sensitive components, including, in particular, enzymes, bleaches and the bleach catalyst. Compositions according to the invention in the form of aqueous solutions or solutions comprising other customary solvents are particularly advantageously prepared by simply mixing the ingredients, which can be added without a diluent or as a solution to an automatic mixer.

To prepare particulate compositions with increased bulk density, in particular in the range from 650 g/l to 950 g/l, a process known from European patent EP 0 486 592 and having an extrusion step is preferred. A further preferred preparation using a granulation process is described in European patent EP 0 642 576. The preparation of compositions according to the invention in the form of non-dusting, storage-stable flowable powders and/or granules with high bulk densities in the range from 800 to 1 000 g/l can also be carried out by, in a first process stage, mixing the builder components with at least some of the liquid mixture components, with an increase in bulk density of this premix, and then, if desired after intermediate drying, combining the other constituents of the composition, including bleach catalyst, with the premix obtained in this way.

To prepare compositions according to the invention in tablet form, preference is given to a procedure which involves mixing all of the constituents together in a mixer and compressing the mixture using conventional tableting presses, for example eccentric presses or rotary presses, using pressing forces in the range from $200 \cdot 10^5$ Pa to $1500 \cdot 10^5$ Pa. This thus gives without problems tablets which are resistant to breakage but which nevertheless dissolve sufficiently rapidly under use conditions and have flexural strengths of normally more than 150 N.

A tablet prepared in this way preferably has a weight of 1–5 g to 40 g, in particular 20 g to 30 g, for a diameter of 3–5 mm to 40 mm.

EXAMPLES

Example 1

Synthesis of 1,2:4,5-di-O-isopropylidene-D-erythro-2,3-hexodiuro-2,6-pyranose 73.6 g of D-fructose were suspended in a mixture of 1.5 of acetone and 30 ml of dimethoxypropane. At 0° C., 15 ml of perchloric acid (70% strength) were added with stirring. After 6 hours at 0° C., the reaction mixture was adjusted to pH 7–8 with ammonium hydroxide, and the solvent was removed. The residue which remained was recrystallized from hexane. Melting point 116–118° C. 10.4 g of the resulting alcohol were dissolved in 200 ml of dichloromethane, and 45 g of molecular sieve (3 A) were added. Then, with stirring, 23 g of PCC, and the mixture was after-stirred for 3 h. Following filtration, the solution was concentrated by evaporation and the residue was recrystallized a number of times from dichloromethane/hexane. The product is obtained as a white solid, melting point: 100–103° C.

Example 2

Synthesis of 1,2:5,6-di-O-isopropylidene-a-D-glucofuranos-3-ulose hydrate. The compound was prepared according to the literature. The melting point is 102–104° C.

Example 3

Synthesis of methyl-3,4-O-isopropylidene-β-L-erythropentopyranosid-2-ulose The compound was prepared according to the literature. The melting point is 90–95° C.

Example 4

Concentration dependency of bleaching to determine the concentration dependency of bleaching, experiments were carried out in a Linitest instrument at 40° C. The test fabric used was tea soiling on cotton (WFK-Krefeld). Caroat® (350 mg/I, Degussa, Frankfurt) was added to 200 ml of wash liquor (2 g/l of P-free WMP laundry detergent (WFK-Krefeld) in water of 150 German hardness). For the individual washing experiments, an increasing concentration of the sugar ketone according to example 1 was added. Washing time: 30 min. Washing temperature: 40° C. The degree of whiteness of the test soiling was determined before and after washing using an Elrepho measuring instrument. As a result, the increase in the degree of whiteness (ΔΔ E) was shown as a function of the ketone concentration:

| Ketone concentration | 0 mg/l | 25 mg/l | 50 mg/l | 100 mg/l |
|---|---|---|---|---|
| ΔΔ E | 0 | 13.1 | 17.5 | 18.5 |

The result shows that even with low concentrations of the sugar ketone according to example 1 excellent bleaching results are obtained.

Example 5 pH Dependency of Bleaching

To determine the pH dependency of bleaching of the sugar ketone according to example 1, washing experiments were carried out at 20° C. in a beaker at a constant pH. Concentration of sugar ketone: 40 mg/l, concentration of Caroat: 350 mg/l. The evaluation was carried out as in example 4.

| | pH | | | | | |
|---|---|---|---|---|---|---|
| | 7 | 8 | 9 | 10 | 11 | 12 |
| Reflectance values ΔΔ E | 0.5 | 10.1 | 15.3 | 15.4 | 7.5 | 1.5 |

The results show that the compound according to the invention has a bleaching optimum in the pH range 8–11.

Example 6

Bleaching Experiments on Curry and Red Wine Soiling

The bleaching effectiveness of the compounds according to the invention of examples 1 to 3 was tested on red wine and curry soiling on cotton (test fabric: WFK-Krefeld) at 20° C. Caroat concentration: 350 mg/L, ketone concentration: 20 mg/L. Washing time 30 min.

| Reflectance values ΔΔ E | | |
|---|---|---|
| Test fabric | Curry/cotton | Red |
| wine/cotton | | |
| Compound according to ex. 1 | 8.3 | 3.6 |
| Compound according to ex. 2 | n.d. | 3.4 |
| Compound according to ex. 3 | n.d. | 3.3 |

The results show a good effectiveness of the ketones according to the invention both on hydrophilic soiling and also on hydrophobic soilings.

Example 5

Example of a denture cleanser formulation

30% by weight of sodium perborate monohydrate
20% by weight of potassium monopersulfate
20% by weight of sodium hydrogencarbonate
5% by weight of sodium carbonate
4% by weight of sodium sulfate
7% by weight of citric acid, sodium salt
1.5% by weight of cyclic sugar ketone according to example 1
1.5% by weight of organic phosphonic acids and salts thereof
4% by weight of polyethylene glycol 20 000
1.5% by weight of polyvinylpyrrolidone
1.5% by weight of Aerosil 200/300
0.75% by weight of sodium dodecylbenzenesulfonate
0.5% by weight of hydrogenated triglycerides
1% by weight of fatty alcohol polyglycol ether
1% by weight of preservative
0.5% by weight of peppermint powder, and
0.25% by weight of Indigotin L-Blue 2 and Quinoline Yellow L-Yellow 3

Said constituents are compressed using known techniques to give a cleaning tablet. In the cleaning test, the formulation exhibits excellent effectiveness.

We claim:

1. A process for enhancing the bleaching action of peroxygen compounds comprising combining the peroxygen compounds with cyclic sugar ketones of the formula

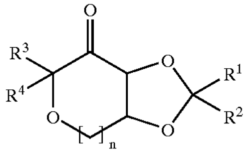

in which $R^1$ and $R^2$ are hydrogen, $C_1$–$C_{22}$-alkyl, $C_2$–$C_{22}$-alkenyl or phenyl, $R^3$ is $C_1$–$C_4$-alkoxy, phenyl-$CH_2$—O— or a group of the formula

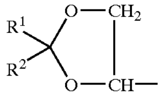

$R^4$ is hydrogen or $R^3$ and $R^4$ together are a group of the formula

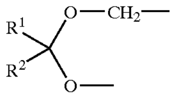

and n is zero or 1, as catalysts for peroxygen compounds.

2. The process of claim 1, wherein the peroxygen compounds are selected from the group consisting of alkali metal peroxosulfates, ammonium peroxosulfates, and mixtures thereof with alkali metal perborate mono- or tetrahydrates and/or alkali metal percarbonates.

3. The process of claim 1, wherein the sugar ketones are selected from the group consisting of 1,2:4,5-di-O-isopropylidene-D-erythro-2,3-hexodiuro-2,6-pyranose, 1,2:4,5-di-O-isopropylidene-L-erythro-2,3-hexodiuro-2,6-pyranose, 1,2:5,6-di-O-isopropylidene-α-D-glucofuranos-3-ulose hydrate, methyl-3,4-O-isopropylidene-β-L-erythropentopyranosid-2-ulose, and mixtures thereof.

4. The process of claim 1, further comprising a compound which releases peroxocarboxylic acid under perhydrolysis conditions.

5. A laundry detergent, bleach or cleaner comprising peroxygen compounds and cyclic sugar ketones as set forth in claim 1.

6. The process of claim 1 wherein the process comprises an effective bleaching temperature less than about 80° C.

7. The process of claim 6 wherein the effective bleaching temperature ranges from about 5° C. to about 45° C.

8. The process of claim 1 further comprising bleach activators containing O- and/or N-acyl groups.

9. The process of claim 1 further comprising bleach activators other than cyclic sugar ketones.

* * * * *